United States Patent
Wu

(10) Patent No.: US 10,039,898 B2
(45) Date of Patent: Aug. 7, 2018

(54) CATHETER SHEATH INTRODUCER WITH DIRECTIONAL RETENTION DAMPER

(71) Applicant: Biosense Webster (Israel), Ltd., Yokneam (IL)

(72) Inventor: Steven Wu, San Jose, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 609 days.

(21) Appl. No.: 13/736,919

(22) Filed: Jan. 8, 2013

(65) Prior Publication Data

US 2014/0194822 A1    Jul. 10, 2014

(51) Int. Cl.
| | | |
|---|---|---|
| *A61M 25/01* | (2006.01) | |
| *A61M 25/00* | (2006.01) | |
| *A61M 25/06* | (2006.01) | |
| *A61B 17/34* | (2006.01) | |
| *A61B 17/00* | (2006.01) | |
| *A61M 25/09* | (2006.01) | |

(52) U.S. Cl.
CPC ..... *A61M 25/0023* (2013.01); *A61B 17/3417* (2013.01); *A61M 25/0068* (2013.01); *A61M 25/0074* (2013.01); *A61M 25/0105* (2013.01); *A61M 25/0662* (2013.01); *A61B 2017/00858* (2013.01); *A61B 2017/347* (2013.01); *A61B 2017/3441* (2013.01); *A61M 25/0075* (2013.01); *A61M 2025/0062* (2013.01); *A61M 2025/09125* (2013.01)

(58) Field of Classification Search
CPC ...... A61M 2025/0062; A61M 25/0023; A61M 25/0021; A61M 25/0075; A61M 2025/006; A61M 25/0032; A61M 2039/0686; F16L 11/121; F16L 9/006

USPC .......................................... 604/171, 172, 264
See application file for complete search history.

(56) References Cited

U.S. PATENT DOCUMENTS 4,601,713 A * 7/1986 Fuqua ........................... 604/514
5,180,364 A * 1/1993 Ginsburg ...................... 604/510
(Continued)

FOREIGN PATENT DOCUMENTS

| CN | 101785901 A | 7/2010 |
|---|---|---|
| CN | 102665608 A | 9/2012 |

(Continued)

OTHER PUBLICATIONS

Extended European Search Report, dated Mar. 28, 2014, for Application No. 14150354.0, 8 pages.
(Continued)

*Primary Examiner* — Kami A Bosworth
*Assistant Examiner* — William Carpenter
(74) *Attorney, Agent, or Firm* — Lewis Roca Rothgerber Christie LLP

(57) ABSTRACT

A catheter sheath introducer comprises a hub and a tubular sheath having an inner lining with one or more dampers to improve retention of medical devices received or passed through the sheath without significantly increasing the force required to advance the medical device through the sheath. The dampers are made of a friction inducing material, for example, rubber-based materials, and configured as fingers, bumps or flaps that are unidirectional by means of an asymmetrical shape relative to a longitudinal axis of the sheath.

12 Claims, 5 Drawing Sheets

(56) References Cited

U.S. PATENT DOCUMENTS

| | | | | |
|---|---|---|---|---|
| 5,209,737 A * | 5/1993 | Ritchart | A61B 17/3462 | |
| | | | 604/167.03 | |
| 5,211,631 A * | 5/1993 | Sheaff | 604/113 | |
| 5,244,619 A * | 9/1993 | Burnham | 264/171.2 | |
| 5,334,169 A * | 8/1994 | Brown et al. | 604/527 | |
| 5,342,315 A * | 8/1994 | Rowe | A61B 17/3462 | |
| | | | 604/167.06 | |
| 5,395,341 A | 3/1995 | Slater | | |
| 5,466,230 A | 11/1995 | Davila | | |
| 5,484,412 A | 1/1996 | Pierpont | | |
| 5,647,846 A * | 7/1997 | Berg et al. | 604/93.01 | |
| 5,681,296 A * | 10/1997 | Ishida | 604/523 | |
| 5,823,961 A * | 10/1998 | Fields et al. | 600/434 | |
| 5,851,189 A * | 12/1998 | Forber | A61M 25/09041 | |
| | | | 600/433 | |
| 6,024,729 A * | 2/2000 | Dehdashtian | A61M 39/0606 | |
| | | | 604/167.04 | |
| 6,117,140 A | 9/2000 | Munsinger | | |
| 6,254,529 B1 * | 7/2001 | Ouchi | A61B 1/00137 | |
| | | | 600/154 | |
| 6,254,626 B1 * | 7/2001 | Dobak et al. | 607/105 | |
| 6,432,091 B1 * | 8/2002 | Davey | 604/246 | |
| 6,520,939 B2 * | 2/2003 | Lafontaine | A61M 39/0606 | |
| | | | 604/167.03 | |
| 6,682,503 B1 * | 1/2004 | Fariss et al. | 604/34 | |
| 6,827,722 B1 * | 12/2004 | Schoenefeld | A61B 17/1622 | |
| | | | 606/104 | |
| 7,727,179 B2 * | 6/2010 | Barrett | 604/27 | |
| 7,927,309 B2 | 4/2011 | Palm | | |
| 7,967,791 B2 * | 6/2011 | Franer | A61B 17/3462 | |
| | | | 604/167.06 | |
| 8,038,628 B2 * | 10/2011 | von Malmborg | A61B 5/0215 | |
| | | | 600/585 | |
| 8,216,295 B2 * | 7/2012 | Benjamin et al. | 623/1.11 | |
| 8,347,880 B2 * | 1/2013 | Tanaka et al. | 128/200.24 | |
| 2001/0049499 A1 * | 12/2001 | Lui | A61M 39/06 | |
| | | | 604/164.05 | |
| 2004/0006305 A1 * | 1/2004 | Hebert et al. | 604/96.01 | |
| 2004/0093061 A1 * | 5/2004 | Acosta et al. | 623/1.11 | |
| 2005/0209674 A1 * | 9/2005 | Kutscher et al. | 623/1.11 | |
| 2009/0259298 A1 * | 10/2009 | Mayberry | A61F 2/07 | |
| | | | 623/1.35 | |
| 2009/0270815 A1 * | 10/2009 | Stamp et al. | 604/249 | |
| 2010/0004730 A1 * | 1/2010 | Benjamin | A61F 2/95 | |
| | | | 623/1.11 | |
| 2011/0137399 A1 | 6/2011 | Chomas et al. | | |

FOREIGN PATENT DOCUMENTS

| | | |
|---|---|---|
| JP | 2000279527 A | 10/2000 |
| JP | 2006522649 A | 10/2006 |
| JP | 2011526815 A | 10/2011 |
| WO | WO 01/64279 A1 | 9/2001 |

OTHER PUBLICATIONS

English translation of SIPO Search Report dated Aug. 9, 2017, issued in corresponding CN 201410007830.7, 3 pages.
English translation of JP Office action dated Sep. 5, 2017, issued in corresponding JP 2014-000790, 6 pages.

* cited by examiner

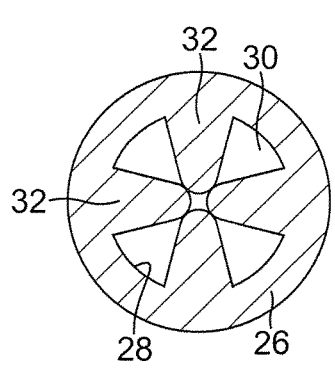 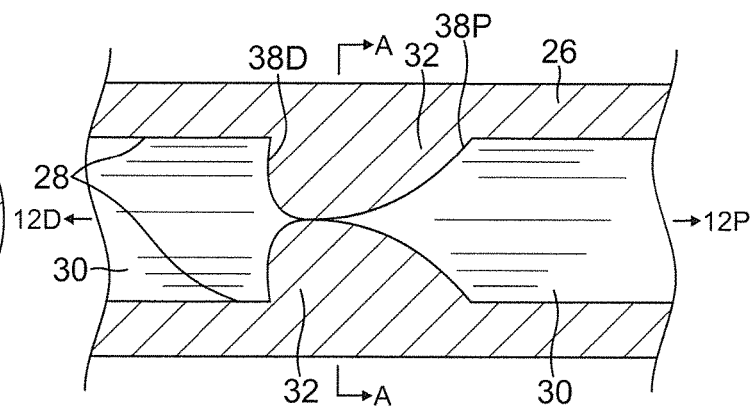
FIG. 6A FIG. 6
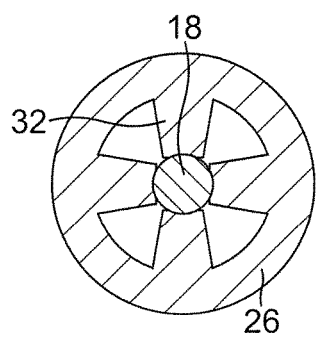 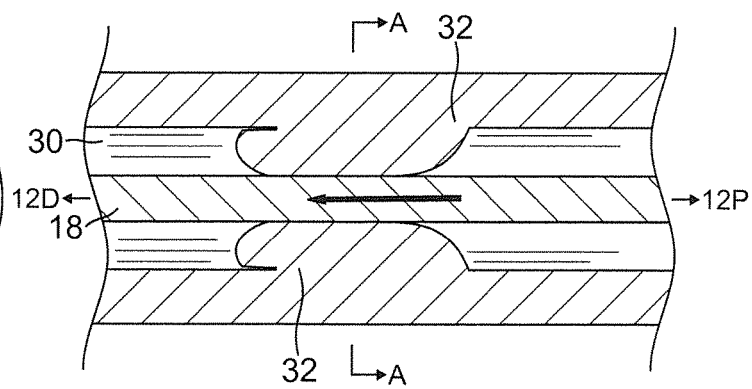
FIG. 7A FIG. 7
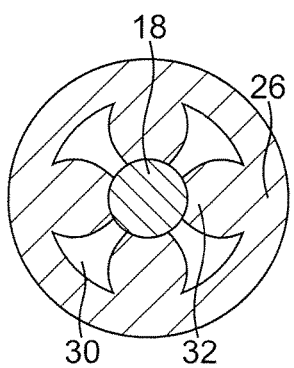 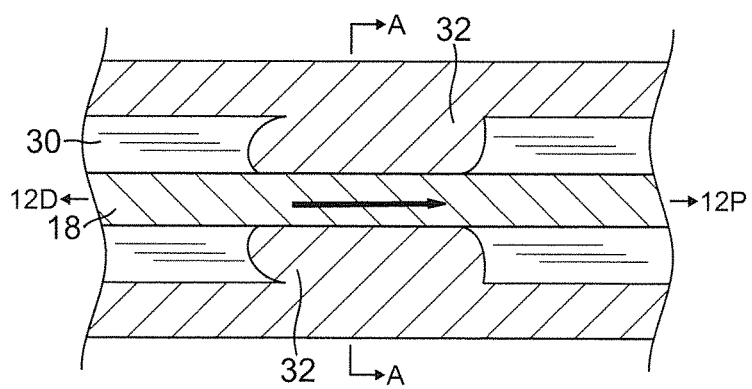
FIG. 8A FIG. 8

CATHETER SHEATH INTRODUCER WITH DIRECTIONAL RETENTION DAMPER

FIELD OF INVENTION

The present invention is directed to a novel catheter sheath introducer.

BACKGROUND

Catheter sheath introducers are well known in the health care industry as a means of providing access to the circulatory system for a number of applications. In a now well know process, the catheter sheath introducer is placed in a desired blood vessel to facilitate various procedures. Among these medical procedures, for example, are mapping, ablation and balloon angioplasty which require the manipulation of catheters through the circulatory system.

Catheter introducers typically include a tubular sheath and a hub attached to a proximal end of the sheath. Throughout a medical procedure, a number of medical devices may be received or fed through the hub and sheath, including a dilator, a guide wire and/or one or more catheters. Catheters especially may have long shafts that require much manipulation to pass through the hub and sheath in order to reach the desired position in the body to effect the medical procedure. However, catheter shafts can slip rotationally and/or longitudinally in the sheath, increasing the effort needed to correctly position the diagnostic or therapeutic distal portion of the catheter within the body.

Accordingly, a need exists for a catheter sheath introducer with improved hold and retention of catheters and other medical devices extending there through without significantly increasing the force required to advance the catheter or medical device through the sheath.

SUMMARY OF THE INVENTION

In accordance with the present invention, a catheter sheath introducer comprising a hub and a tubular sheath having an inner lining with one or more dampers is provided. The dampers are unidirectional so as to improve retention of medical devices received or passed through the sheath without significantly increasing the force required to advance the medical device through the sheath.

In one embodiment, the dampers extend from an inner circumferential lining of the sheath and project inwardly in a lumen of the sheath so as to contact a medical device received in or passed through the lumen of the sheath. The dampers are made of a friction inducing material, for example, rubber-based materials, and configured as fingers, bumps or flaps that are unidirectional by means of an asymmetrical shape relative to a longitudinal axis of the sheath so that the medical device encounters less frictional impedance when being advanced distally relative to the sheath and more frictional impedance with being withdrawn proximally relative to the sheath.

A more detailed explanation of the invention is provided in the following description and claims and is illustrated in the accompanying drawings.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 6 is an enlarged side cross-sectional view of dampers in accordance with another embodiment, engaged with a medical device being advanced distally through a sheath.

FIG. 6A is an end cross-sectional view of the dampers and medical device of FIG. 6, taken along line A-A.

FIG. 7 is an enlarged side cross-sectional view of the dampers of FIG. 6, engaged with a medical device being advanced distally through the sheath.

FIG. 7A is an end cross-sectional view of the dampers and medical device of FIG. 7, taken along line A-A.

FIG. 8 is an enlarged side cross-sectional view of the dampers of FIG. 6 applying a retention force on the medical device.

FIG. 8A is an end cross-sectional view of the dampers and medical device of FIG. 8, taken along line A-A.

DETAILED DESCRIPTION OF THE INVENTION

Figure 1:
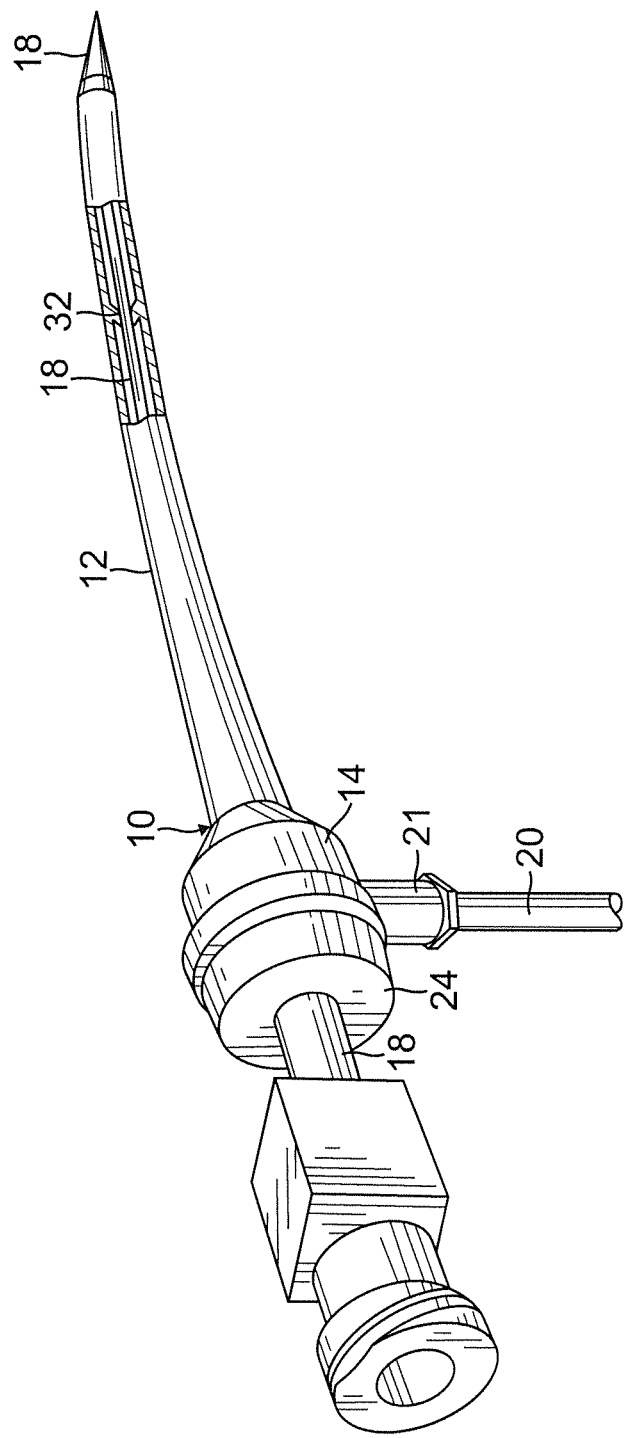
FIG. 1 is a perspective view of a catheter sheath introducer of the present invention in accordance with one embodiment.
Figure 2:
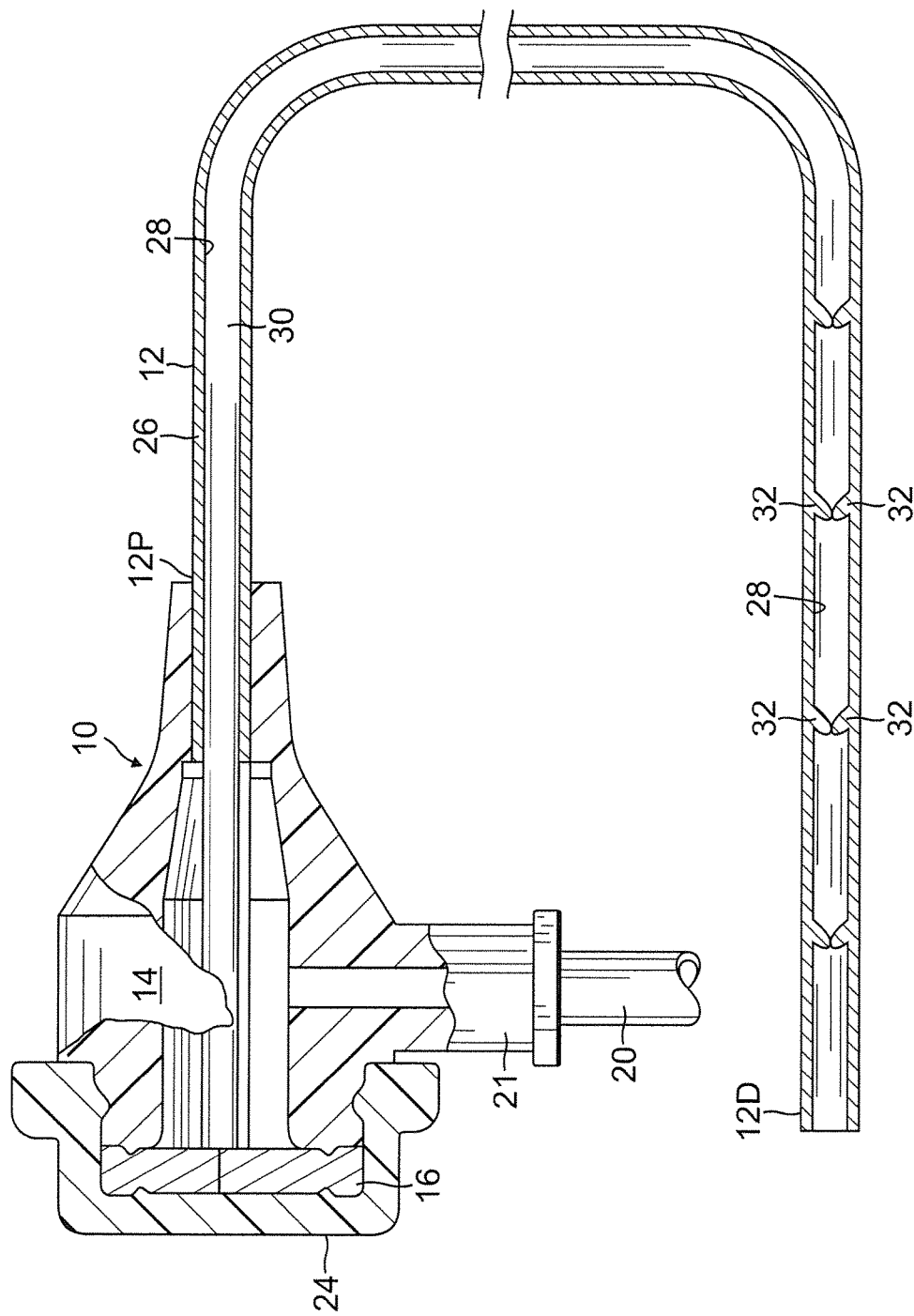
FIG. 2 is an elevational view, with portions broken away, of the catheter sheath introducer of FIG. 1.

Referring to the drawings, FIGS. 1 and 2 show a catheter sheath introducer 10 having a tubular sheath 12 and a hub 14. The sheath 12 has a distal end 12D and a proximal end 12P, and the hub 14 is attached to the proximal end 12D. The catheter sheath introducer 10 also includes a hemostasis valve 16 to provide sealing of the sheath around a medical device 18, e.g., a dilator unit. A branch conduit 20 and a locking sleeve 21 off of hub 14 are provided to allow for, among other things, connections to saline solution or medicines and access to other medical procedures. An end cap 24 is provided at the proximal end of hub 14. A guide wire 22 is also shown as it is often used with such devices as balloon angioplasty catheters.

FIG. 2 shows the catheter sheath introducer 10 cut away to expose some of the internal structure. The sheath 12 is joined to the internal body of hub 14. The sheath 12 is a tubular structure with at least one layer 26 providing an inner circumferential surface or lining 28 surrounding a lumen 30. The layer 26 be constructed of any suitable material that is sufficiently pliant, elastic, flexible and friction-inducing with medical devices extending through the sheath 12. Suitable materials include rubber-based materials, e.g., silicon rubber, or a thermoplastic elastomer, or extrudable tacky plastic, e.g., polyethylene, polypropylene.

Figure 3A:
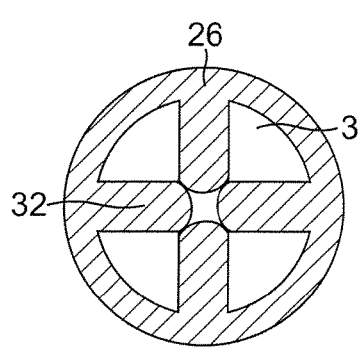
FIG. 3A is an end cross-sectional view of the dampers of FIG. 3, taken along line A-A.
Figure 3:
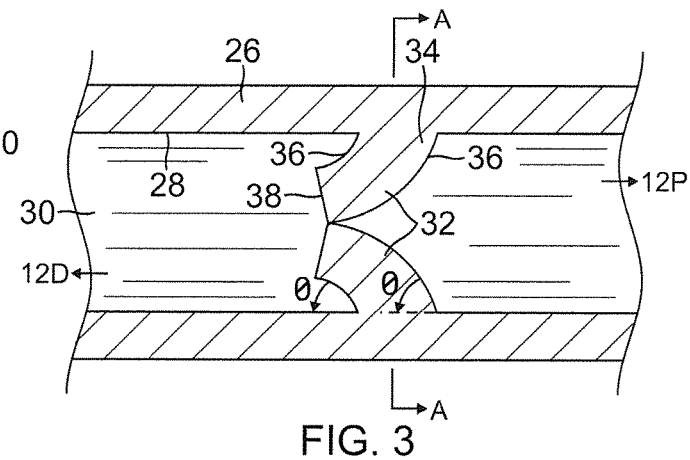
FIG. 3 is an enlarged side cross-sectional view of dampers within a sheath of FIG. 2.

In accordance with a feature of the present invention, one or more dampers 32 are formed on in inner surface 28 of the sheath 12. The dampers 32 include raised formations that project inwardly from into lumen 30 to at least partially occlude the lumen 30. In the embodiment of FIGS. 2, 3 and 3A, the dampers 32 are configured like "fingers", each with a base 34, two generally parallel side edges 36 and an unattached outer edge 38. In the illustrated embodiment, the dampers 32 are arranged in diametrical pairs that oppose each other in the lumen 30 and equally spaced from each other around the circumference and each damper has a generally uniform thickness. When the lumen 30 is empty, each pair of dampers 32 are in their neutral configuration with the outer edges 38 of one or more pairs of dampers being in contact with each other, although it is understood that equal spacing and contact are not necessary in every embodiment of the present invention. In the neutral configuration, the dampers 32 point toward the distal end 12D of the sheath where each side edge 36 defines an inner angle θ ranging between about 0 and less than 90 degrees, preferably between about 20 and 60 degrees and more preferably about 45 degrees, relative to the inner surface 28 of the sheath 12. Each damper 32 has a length such that at least a distal portion of each damper is distal of the base 34 of the respective damper. The plurality of dampers may vary as needed or desired. In one embodiment, the plurality ranges between about two and six, and more preferably about three or four.

Figure 4A:
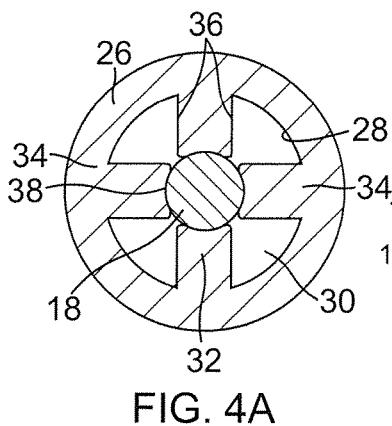
FIG. 4A is an end cross-sectional view of the dampers and medical device of FIG. 4, taken along line A-A.
Figure 4:
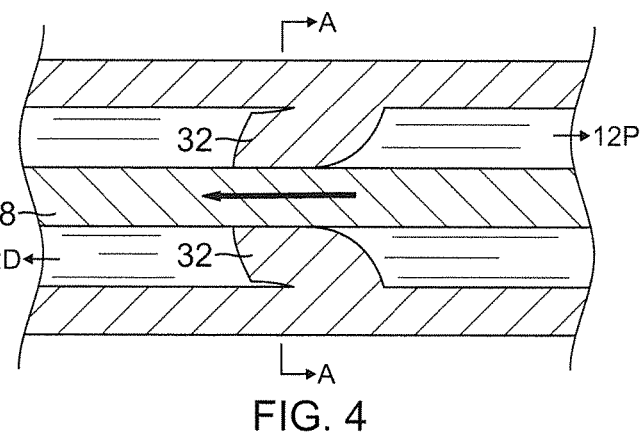
FIG. 4 is an enlarged side cross-sectional view of the dampers of FIG. 2, engaged with a medical device being advanced distally through the sheath.
Figure 5A:
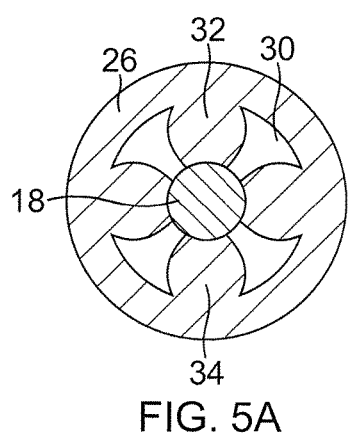
FIG. 5A is an end cross-sectional view of the dampers and medical device of FIG. 5, taken along line A-A.
Figure 5:
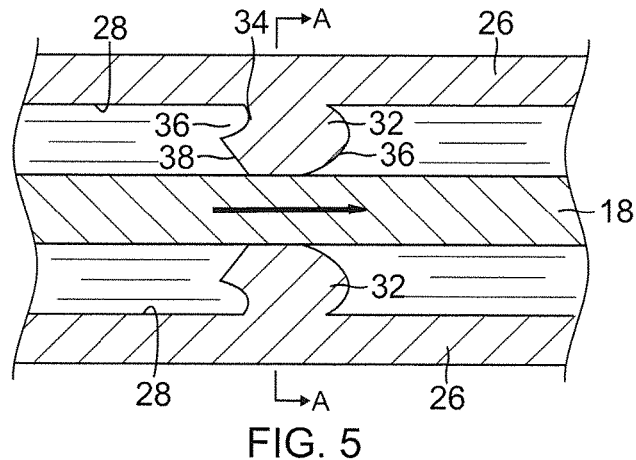
FIG. 5 is an enlarged side cross-sectional view of the dampers of FIG. 2 applying a retention force on the medical device.
Figure 9A:
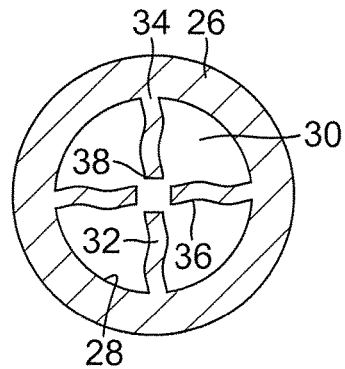
FIG. 9A is an end cross-sectional view of the dampers and medical device of FIG. 9, taken along line A-A.
Figure 9:
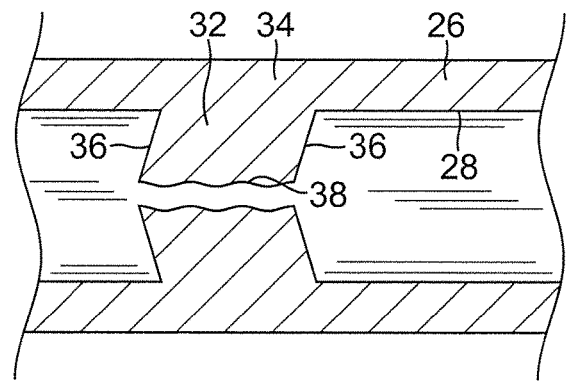
FIG. 9 is an enlarged side cross-sectional view of dampers in accordance with yet another embodiment, engaged with a medical device being advanced distally through a sheath.
Figure 10A:
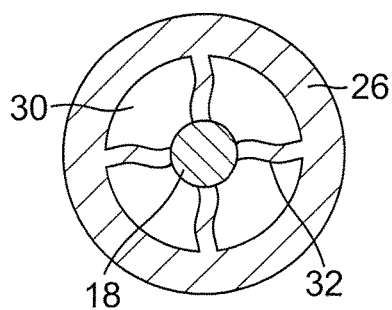
FIG. 10A is an end cross-sectional view of the dampers and medical device of FIG. 10, taken along line A-A.
Figure 10:
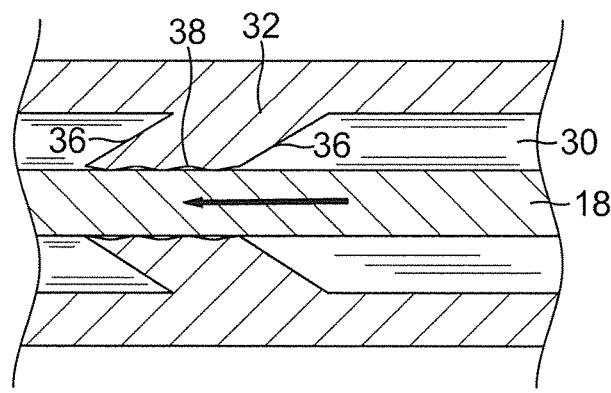
FIG. 10 is an enlarged side cross-sectional view of the dampers of FIG. 9, engaged with a medical device being advanced distally through the sheath.
Figure 11A:
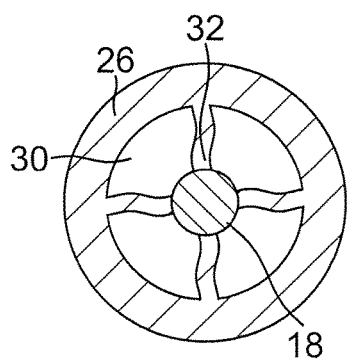
FIG. 11A is an end cross-sectional view of the dampers and medical device of FIG. 11, taken along line A-A.
Figure 11:
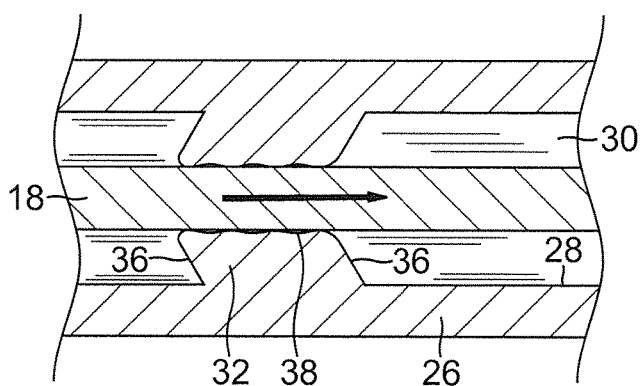
FIG. 11 is an enlarged side cross-sectional view of the dampers of FIG. 9 applying a retention force on the medical device.

When a user advances a medical device 18 through the lumen (FIGS. 4 and 4A), the medical device comes into contact with one or more dampers 32. Angled distally, the dampers deform, e.g., elongating and/or becoming further distally angled, under the advancing force of the device 18 and allow further distal advancement of the device 18 through the lumen 30.

When the medical device 18 is released by the user, elasticity of the dampers 32 aided by their friction-inducing property causes the dampers to at least initially shorten and thicken before stabilizing in a compressed state thereby providing a retention force acting on the device 18 to hold it in place. The retention force prevents slippage of the medical device in terms of rotational and/or longitudinal movement that may be caused by other forces acting on the device, including the body's circulatory system and/or deformation/elasticity of the device itself due to kinks or bends along its length. The retention force is sufficient to hold the device 18 in place but a relatively low static coefficient of friction provided by the dampers against the device 18 allows the device to be withdrawn proximally when actively pulled by the user. The unidirectional geometry of the dampers 32 by means of their shape and configuration allows the sheath introducer 10 to provide "hands-free" utility so that the user need not maintain a hand on the device at all times while the device is inside the sheath introducer.

In an alternate embodiment as illustrated in FIGS. 6 and 6A, the dampers 32 are configured as "bumps" with greater radial and circumferential thicknesses compared to the above-described "finger" dampers. The thickness may be uniform and/or nonuniform in the radial and/or circumferential direction. In the illustrated embodiment, the thickness in the radial direction is tapered, that is, thicker at the base 34 and thinner at an outer edge 38. Compared to the "finger" dampers, the "bump" dampers may have a more curved profile. However, the bump dampers are also unidirectional in that the curved profile is angled distally, where the outer edge has a more linear proximal portion 38P and a more curved distal portion 38D.

In another alternate embodiment as illustrated in FIGS. 7 and 7A, the dampers 32 are configured as "flaps" with a lesser radial thickness but a thicker base 34. The dampers are also unidirectional and thus are angled toward the distal end 12D of the sheath. Both side edges 36 form an angle θ, as defined above.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Some features are exaggerated for purposes of discussion. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter sheath introducer adapted for use with a medical device, comprising:
   a hub;
   an elongated sheath comprising a tubular structure with a distal end and a proximal end, the tubular structure having at least one layer with an inner circumferential surface defining a lumen, the hub connected to the proximal end of the sheath, the elongated sheath being flexible such that the elongated sheath is insertable into and bendable within a patient's vasculature; and
   a plurality of damper sets, each of the plurality of damper sets being located distal of a distal end of the hub and comprising four circumferentially aligned dampers aligned along a same circumference of the inner circumferential surface and arranged in two diametrically opposing pairs, the circumferentially aligned dampers extending inwardly from the inner circumferential surface, each of the circumferentially aligned dampers comprising a base in contact with the inner circumferential surface of the elongated sheath and a free distal end, the bases of the circumferentially aligned dampers of each of the plurality of damper sets being spaced from each other along the same circumference of the inner circumferential surface and the free distal ends of at least two of the circumferentially aligned dampers of each of the plurality of damper sets being in contact with each other when the circumferentially aligned dampers are in a neutral position,
   wherein the distal end of one of the circumferentially aligned dampers of one of the diametrically opposing pairs is in contact with the distal end of another of the circumferentially aligned dampers of the same diametrically opposing pair when the circumferentially aligned dampers are in the neutral position, the circumferentially aligned dampers each having a unidirectional configuration and being biased toward the neutral position;

wherein the plurality of damper sets is configured to contact and apply a retention force on the medical device received in the lumen of the elongated sheath, the retention force being applied to hold the medical device in a selected position relative to the sheath and to resist unintentional rotational and longitudinal movement from the selected position, the circumferentially aligned dampers being configured to deform upon contacting the medical device, and the circumferentially aligned dampers defining an open passage when the circumferentially aligned dampers are in the neutral position.

2. The catheter sheath introducer of claim 1, wherein the circumferentially aligned dampers are constructed of a rubber-based material.

3. The catheter sheath introducer of claim 2, wherein the circumferentially aligned dampers are formed from the at least one layer of the tubular structure.

4. The catheter sheath introducer of claim 1, wherein the circumferentially aligned dampers are angled distally.

5. The catheter sheath introducer of claim 1, wherein the circumferentially aligned dampers are configured as fingers.

6. The catheter sheath introducer of claim 1, wherein the circumferentially aligned dampers are configured as bumps.

7. The catheter sheath introducer of claim 1, wherein the distal end of at least one of the circumferentially aligned dampers of one of the diametrically opposing pairs is in contact with the distal end of at least one of the circumferentially aligned dampers of another of the diametrically opposing pairs when the circumferentially aligned dampers are in the neutral position.

8. The catheter sheath introducer of claim 1, wherein each circumferentially aligned damper has at least one edge that forms an inner angle with the inner circumferential surface of the elongated sheath toward the distal end of the tubular structure, the inner angle being less than about 90 degrees.

9. A catheter sheath introducer adapted for use with a medical device, comprising:
a hub;
an elongated sheath comprising a tubular structure with a distal end and a proximal end, the tubular structure having at least one layer with an inner circumferential surface defining a lumen, the hub connected to the proximal end of the sheath, the elongated sheath being flexible such that the elongated sheath is insertable into and bendable within a patient's vasculature; and
a plurality of damper sets, each of the plurality of damper sets being located distal of a distal end of the hub and comprising four circumferentially aligned dampers aligned along a same circumference of the inner circumferential surface and arranged in two diametrically opposing pairs, the circumferentially aligned dampers extending radially inward from the inner circumferential surface, the circumferentially aligned dampers each configured as fingers comprising a base in contact with the inner circumferential surface of the elongated sheath and a free distal end, the bases of the circumferentially aligned dampers of each of the plurality of damper sets being spaced from each other along the same circumference of the inner circumferential surface and the free distal ends of at least two of the circumferentially aliened dampers of each of the plurality of damper sets being in contact with each other when the circumferentially aligned dampers are in a neutral position, wherein the distal end of one of the circumferentially aligned dampers of one of the diametrically opposing pairs is in contact with the distal end of another of the circumferentially aligned dampers of the same diametrically opposing pair when the circumferentially aligned dampers are in the neutral position, and the circumferentially aligned dampers each having a unidirectional configuration and being biased toward the neutral position, wherein the plurality of damper sets is configured to contact and apply a retention force on the medical device received in the lumen of the elongated sheath, the retention force being applied to hold the medical device in a selected position relative to the sheath and to resist unintentional rotational and longitudinal movement from the selected position, the circumferentially aligned dampers being configured to deform upon contacting the medical and the circumferentially aligned dampers defining an open passage when the circumferentially aligned dampers are in the neutral position.

10. The catheter sheath introducer of claim 9, wherein each circumferentially aligned damper has at least one edge that forms an inner angle with the inner circumferential surface of the elongated sheath toward the distal end of the tubular structure, the inner angle being less than about 90 degrees.

11. A catheter sheath introducer adapted for use with a medical device, comprising: a hub;
an elongated sheath comprising a tubular structure with a distal end and a proximal end, the tubular structure having at least one layer with an inner circumferential surface defining a lumen, the hub connected to the proximal end of the sheath, the elongated sheath being flexible such that the elongated sheath is insertable into and bendable within a patient's vasculature; and
a plurality of damper sets, each of the plurality of damper sets being located distal of a distal end of the hub and comprising four circumferentially aligned dampers aligned along a same circumference of the inner circumferential surface and arranged in two diametrically opposing pairs, the circumferentially aligned dampers extending inward from the inner circumferential surface, each of the circumferentially aligned dampers comprising a base in contact with the inner circumferential surface of the elongated sheath and a free distal end, the bases of the circumferentially aligned dampers being spaced from each other along the same circumference of the inner circumferential surface and the free distal ends of at least two of the circumferentially aligned dampers of each of the plurality of damper sets being in contact with each other when the circumferentially aligned dampers are in a neutral position,
wherein the distal end of one of the circumferentially aligned dampers of one of the diametrically opposing pairs is in contact with the distal end of another of the circumferentially aligned dampers of the same diametrically opposing pair when the circumferentially aligned dampers are in the neutral position, the circumferentially aligned dampers each having a same unidirectional configuration and being biased toward the neutral position;

wherein the plurality of damper sets is configured to contact and apply a retention force on the medical device received in the lumen of the elongated sheath, the retention force being applied to hold the medical device in a selected position relative to the sheath and to resist unintentional rotational and longitudinal movement from the selected position, the circumferentially aligned dampers being configured to deform upon contacting the medical device, and the circumferentially aligned dampers defining an open passage when the circumferentially aligned dampers are in the neutral position.

12. The catheter sheath introducer of claim 11, wherein each circumferentially aligned damper has at least one edge that forms an inner angle with the inner circumferential surface of the elongated sheath toward the distal end of the tubular structure, the inner angle being less than about 90 degrees.

\* \* \* \* \*